(12) United States Patent
Ichihara et al.

(10) Patent No.: US 9,284,326 B2
(45) Date of Patent: Mar. 15, 2016

(54) METHOD FOR PRODUCING EPOXY COMPOUND

(71) Applicants: JX Nippon Oil & Energy Corporation, Tokyo (JP); OSAKA UNIVERSITY, Suita-shi, Osaka (JP)

(72) Inventors: Junko Ichihara, Suita (JP); Shunro Yamaguchi, Suita (JP); Atsushi Kameyama, Tokyo (JP); Takashi Suzuki, Tokyo (JP); Takashi Morikita, Tokyo (JP)

(73) Assignees: JX Nippon Oil & Energy Corporation, Tokyo (JP); OSAKA UNIVERSITY, Suita-shi, Osaka (JP)

( * ) Notice: Subject to any disclaimer, the term of this patent is extended or adjusted under 35 U.S.C. 154(b) by 0 days.

(21) Appl. No.: 14/402,394

(22) PCT Filed: Apr. 26, 2013

(86) PCT No.: PCT/JP2013/062356
§ 371 (c)(1),
(2) Date: Nov. 20, 2014

(87) PCT Pub. No.: WO2013/175937
PCT Pub. Date: Nov. 28, 2013

(65) Prior Publication Data
US 2015/0094479 A1 Apr. 2, 2015

(30) Foreign Application Priority Data
May 22, 2012 (JP) ................ 2012-116390

(51) Int. Cl.
*C07D 303/00* (2006.01)
*C07D 493/04* (2006.01)
*C07D 301/12* (2006.01)

(52) U.S. Cl.
CPC ............ *C07D 493/04* (2013.01); *C07D 301/12* (2013.01)

(58) Field of Classification Search
CPC ..... C07D 493/04; C07D 301/12; B01J 23/30; B01J 31/34
USPC ......................................... 549/544
See application file for complete search history.

(56) References Cited

U.S. PATENT DOCUMENTS 5,430,161 A * 7/1995 Brown et al. ................ 549/531
2010/0113807 A1 5/2010 Ichihara et al.

FOREIGN PATENT DOCUMENTS

| JP | S62-234550 A | 10/1987 |
| JP | 2003-238545 A | 8/2003 |
| JP | 2010-235649 A | 10/2010 |
| WO | 2008093711 A1 | 8/2008 |

OTHER PUBLICATIONS

Okovytyy et al, "Identification of the stereoisomers of tetrahydroindene diepoxide by the 1H and 13C NMR characteristics: A combined experimental and theoretical study," Journal of Molecular Structure: Theochem, vol. 730, No. 1-3, pp. 125-132 (2005).
Matoba et al, "Epoxidation of cyclic diolefins with hydrogen peroxide catalyzed by areneseleninic acid," Journal of Japan Petroleum Institute, vol. 26, No. 5, pp. 349-354 (1983).
Int'l Search Report issued Jun. 11, 2013 in Int'l Application No. PCT/JP2013/062356.

* cited by examiner

*Primary Examiner* — T. Victor Oh
(74) *Attorney, Agent, or Firm* — Panitch Schwarze Belisario & Nadel LLP

(57) ABSTRACT

The present invention provides a method for producing an epoxy compound by expoxidation of an olefin compound with good productivity wherein a compound having a carbon-carbon double bond is reacted with hydrogen peroxide in the coexistence of (a) a compound having a carbon-carbon double bond, (b) a hydrogen peroxide solution, (c) a powdered solid catalyst support and (d) a powdered catalyst and optionally (e) an organic solvent, the total mass of (c) and (d) being 100 percent by mass or less on the basis of the total mass of (a), (b) and (e).

8 Claims, No Drawings

METHOD FOR PRODUCING EPOXY COMPOUND

CROSS-REFERENCE TO RELATED APPLICATION

This application is a Section 371 of International Application No. PCT/JP2013/062356, filed Apr. 26, 2013, which was published in the Japanese language on Nov. 28, 2013, under International Publication No. WO 2013/175937 A1, and the disclosure of which is incorporated herein by reference.

TECHNICAL FIELD

The present invention relates to a method for producing an epoxy compound from an olefin compound and hydrogen peroxide.

BACKGROUND ART

Epoxy compounds are reacted with various curing agents and curing catalysts to produce cured products. These epoxy compounds are useful as components of coating agents, adhesives, inks or sealants or intermediates for producing compounds which are useful in the various final applications such as pharmaceutical agents or medical products.

As a method for producing an epoxy compound, a method is known, in which olefins are oxidized with peracids such as peracetic acid. However, this method has problems that peracids require careful handling, epoxides are reacted with carboxylic acids present in the reaction system thereby producing esters and the like, resulting in a decrease in the selectivity of the epoxides and the post-treatments are troublesome. Therefore, a method has been attracting attention, which uses hydrogen peroxide as an oxidation agent, which is easy in handling and turns to water that is harmless after the reaction.

As a method for producing an epoxy compound from olefins using hydrogen peroxide, a method is known in which epoxidation is carried out by reacting olefins and a hydrogen peroxide solution with a halogenated hydrocarbon as a solvent using a catalyst such as polyacids (Patent Literature 1). This method, however, has problems concerning halogen impurities in the products and environmental load due to the use of the halogenated hydrocarbon.

Patent Literature 2 discloses a solid phase reaction system for oxidation comprising a mixture of a powdered solid catalyst support and a powdered solid catalyst for oxidation reaction, an organic compound and a hydrogen peroxide solution.

CITATION LIST

Patent Literature

Patent Literature 1: Japanese Patent Application Laid-Open Publication No. 62-234550
Patent Literature 2: WO2008/093711

SUMMARY OF INVENTION

Technical Problem

The present invention has an object to provide a method for carrying out epoxidation of an olefin compound with good productivity.

Solution to Problem

The present invention has been accomplished as the results of extensive studies to achieve the above object.

That is, the present invention relates to a method for producing an epoxy compound by reacting a compound having a carbon-carbon double bond with hydrogen peroxide in the coexistence of (a) a compound having a carbon-carbon double bond, (b) a hydrogen peroxide solution, (c) a powdered solid catalyst support and (d) a powdered catalyst and optionally (e) an organic solvent wherein the total mass of (c) and (d) is 100 percent by mass or less on the basis of the total mass of (a), (b) and (e).

The present invention also relates to the foregoing method for producing an epoxy compound wherein the amount of the organic solvent is from 0 to 500 percent by mass on the basis of the amount of the compound having a carbon-carbon double bond.

The present invention also relates to the foregoing method for producing an epoxy compound wherein the solid catalyst is selected from the group consisting of: oxides of metals selected from the group consisting of tungsten, molybdenum and vanadium; oxoacids containing metals selected from the group consisting of tungsten, molybdenum and vanadium and salts thereof; and oxides, halides and sulfates of elements selected from the group consisting of iron, manganese and ruthenium.

The present invention also relates to the foregoing method for producing an epoxy compound wherein the solid catalyst is selected from the group consisting of oxides of tungsten or molybdenum, isopolyacids containing tungsten or molybdenum and heteropolyacids containing tungsten or molybdenum and particularly relates to the foregoing method for producing an epoxy compound wherein the solid catalyst is an isopolyacid containing tungsten.

The present invention also relates to the foregoing method for producing an epoxy compound wherein the solid catalyst support is selected from the group consisting of phosphates, diatomaceous earth, silica, alumina, kaolin, silica-alumina and calcium fluoride and particularly relates to the foregoing method for producing an epoxy compound wherein the solid catalyst support is apatite.

Advantageous Effect of Invention

The method for producing an epoxy compound of the present invention can produce an epoxy compound from a compound having a carbon-carbon double bond at a higher reaction rate and yield and has advantages that it can reduce environmental loads caused by wastewater treatment. Furthermore, the method has advantages that isolation or recovery of the product is easily carried out, and thus is a method for producing an epoxy compound with a high industrial value.

DESCRIPTION OF EMBODIMENTS

Preferable embodiments of the present invention will be described below.

The present invention relates to a method for producing an epoxy compound by reacting a compound having a carbon-carbon double bond with hydrogen peroxide in the coexistence of (a) a compound having a carbon-carbon double bond, (b) a hydrogen peroxide solution, (c) a powdered solid catalyst support and (d) a powdered catalyst and optionally (e) an organic solvent wherein the total mass of (c) and (d) is 100 percent by mass or less on the basis of the total mass of (a), (b) and (e).

The method of the present invention produces an epoxy compound by preparing a slurry by mixing a mixture of (c) a powdered solid catalyst support and (d) a powdered catalyst with (a) a compound having a carbon-carbon double bond and (b) a hydrogen peroxide solution and optionally (e) an organic solvent and then allowing the components to contact with one another in the slurry to oxidize the compound having a carbon-carbon double bond.

The method of the present invention does not use peracid unlike methods as disclosed in Patent Literature 1 and thus can simplify the post-treatment and significantly reduce environmental loads. Furthermore, since no carboxylic acid is present in the system, the method can suppress the production of esters and alcohols and thus is higher in epoxidation selectivity. Furthermore, although a conventional method using peracid has a problem that in production of an alicyclic epoxy compound regarded as having a high reactivity with acids, coexisting organic acids are easily reacted with epoxy groups produced in the presence of water, resulting in a decrease in the selectivity of the epoxides due to the ring-opening of the epoxy groups, the present invention has solved the problem. Furthermore, the method of the present invention is higher in selectivity of a diepoxy compound in an oxidation reaction and needs no complicated treatment process, thereby making it possible to recover the diepoxy compound without production loss.

No particular limitation is imposed on the compound having a carbon-carbon double bond used in the present invention if it is a compound having one or more carbon-carbon double bonds per molecule.

Examples of such a compound include monosubstituted olefins such as ethylene, propylene, 1-butene, 1-pentene, 4,4-dimethyl-1-pentene, 1-hexene, 1-heptene, 1-octene, 1-nonene, 1-decene, 1-undecene, 1-dodecene, 1-tridecene, 1-tetradecene, 1-pentadecene, 1-hexadecene, 1-octadecene, 3,3-dimethyl-1-butene, vinylcyclopentane, vinylcyclohexane, allylcyclohexane, styrene, 4-(tert-butyl)styrene, allylbenzene, 4-methoxystyrene, safrole, eugenol, and 3,4-dimethoxy-1-allylbenzene;

disubstituted olefins such as 2-butene, isobutylene, 2-methyl-1-butene, 2-pentene, 2-hexene, 2-methyl-1-hexene, 3-hexene, 2-heptene, 2-methyl-1-heptene, 3-heptene, 2-octene, 3-octene, 4-octene, 2-nonene, 2-methyl-2-nonene, 3-nonene, 4-nonene, 5-decene, 2-methyl-1-undecene, cyclopentene, cyclohexene, 4-methylcyclohexene, cycloheptene, cyclooctene, cyclodecene, cyclododecene, methylenecyclohexane, β-methylstyrene, stilbene, isosafrole, isoeugenol, β-pinene and norbornene;

trisubstituted olefins such as 2-methyl-2-butene, 2-methyl-2-pentene, 2-methyl-2-hexene, 2,5-dimethyl-2,4-hexadiene, 2-methyl-2-heptene, 1-methylcyclopentene, 1-methylcyclohexene, 1-(tert-butyl)cyclohexene, 1-isopropylcyclohexene, 2-carene, 3-carene and α-pinene; and tetrasubstituted olefins such as 2,3-dimethyl-2-butene and 2,3,4-trimethyl-2-pentene.

Alternatively, in the present invention, other than the above-described olefin compounds, alicyclic olefin compounds represented by formula (2) below are also preferably used:

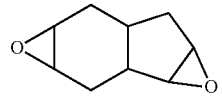

In formula (2), $R^1$, $R^2$, $R^3$, $R^4$, $R^5$, $R^6$, $R^7$, $R^8$, $R^9$, $R^{10}$, $R^{11}$ and $R^{12}$ are each independently hydrogen, halogen, an alkyl group which may have a substituent or an alkoxy group which may have a substituent.

The alkyl group is preferably an alkyl group having 1 to 10 carbon atoms, more preferably an alkyl group having 1 to 4 carbon atoms. When the alkyl group has a substituent, examples thereof include halogens and alkoxy groups.

The alkoxy group is preferably an alkoxy group having 1 to 10 carbon atoms, more preferably an alkoxy group having 1 to 4 carbon atoms. when the alkoxy group has a substituent, examples thereof include halogens and alkoxy groups.

$R^1$ to $R^{12}$ are each independently preferably, hydrogen, fluorine, an alkyl group or an alkoxy group, more preferably hydrogen or fluorine, more preferably hydrogen.

That is, the alicyclic olefin compound represented by formula (2) is preferably a compound represented by formula (3) below from which an alicyclic diepoxy compound represented by formula (1) below can be produced through oxidation reaction.

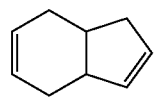

(3)

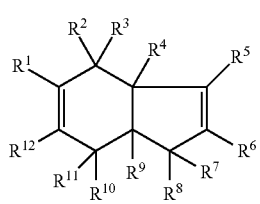

(1)

The solid catalyst support may be powders of solid materials having properties that they disperse a solid catalyst, a hydrogen peroxide solution and a compound having a carbon-carbon double bond, are not degraded thereby and do not disturb the oxidation reaction, preferably those having properties to facilitate the oxidation reaction. Specific examples include phosphates such as apatite, clays such as diatomaceous earth [main component: silica], kaolin [main component: silica-alumina] and hydrotalcite, fluorides such as calcium fluoride, and oxides such as silica, titania and alumina. Among these, a solid catalyst support selected from phosphates, diatomaceous earth, silica, alumina, kaolin, silica-alumina and calcium fluoride is preferably used because they can achieve a higher yield. In particular, a solid catalyst support selected from apatite, diatomaceous earth and calcium fluoride can achieve a particularly higher yield.

Herein, the apatite is a kind of calcium phosphate, and fluorapatite, chlorapatite, carbonate apatite and hydroxyapatite exist as apatite-type minerals. Among these, hydroxyapatite and fluorapatite are preferably used.

The diatomaceous earth is a soft rock or soil composed mainly of a husk of Bacillariophyta, and contains silica as a main component but also often alumina, ferric oxide, alkali metal oxides in addition to silica. Alternatively, those which are porous and have a high porosity and a cake bulk density of about 0.2 to 0.45 are often used. Among diatomaceous earths, calcined products or freshwater diatomaceous earths are preferred but other diatomaceous earths may be used. Specific examples of such diatomaceous earths include those marketed under the tradename of Celite (registered trademark) by Celite Corporation and marketed under the tradename of Celatom by Eagle Pitcher Minerals, Inc. Alternatively, those calcined together with sodium carbonate may also be used.

Examples of the solid catalyst include: oxides of metals selected from the group consisting of tungsten, molybdenum and vanadium; oxoacids containing metals selected from the group consisting of tungsten, molybdenum and vanadium and salts thereof; and oxides, halide and sulfates of elements selected from the group consisting of iron, manganese and ruthenium.

Examples of the oxides of metals selected from the group consisting of tungsten, molybdenum and vanadium include $WO_3$, $MoO_3$ and $V_2O_5$. Examples of the oxoacids containing metals selected from the group consisting of tungsten, molybdenum and vanadium and salts thereof include tungstic acid ($H_2WO_4$) and tungstates such as $Na_2WO_4$, molybdenum acid ($H_2MoO_4$) and molybdates such as $Na_2MoO_4$, vanadic acid and vanadates such, as $NH_4VO_3$, isopolyacids containing tungsten, molybdenum or vanadium and salts thereof, and heteropolyacids containing tungsten, molybdenum or vanadium and salts thereof. Isopolyacids or heteropolyacids containing tungsten, molybdenum or vanadium also include mixtures represented by $Q_3[PW_6Mo_6O_{40}]$ and $Q_7[PV_4Mo_8O_{40}]$ and peroxo-type compounds represented by $Q_3\{PO_4[W(O)(O_2)]_4\}$ and $Q_2[W_2O_3(O_2)_4]$ (in these formulae, Q represents a counter cation).

Examples of the hetero atom of the heteropolyacids include phosphorus, boron, silicone, germanium, lanthanoid elements, manganese, nickel, iron, cobalt or ruthenium. Examples of the counter cations of the isopolyacid salts or heteropolyacid salts include organic cations such as tetrabutylammonium, butylammonium, benzyltrimethylammonium, cetyltrimethylammonium and cetylpyridinium and inorganic cations such as ammonium, potassium, sodium and calcium.

More specifically, examples of the isopolytungstic acids containing tungsten include $(NH_4)_6W_7O_{24}$, $(NH_4)_{10}[H_2W_{12}O_{42}]$, $(CetylNMe_3)_7(NH_4)_3[H_2W_{12}O_{42}]$, $(CetylNMe_3)_{10}[H_2W_{12}O_{42}]$, $(CetylPy)_9(NH_4)[H_2W_{12}O_{42}]$, $(CetylPy)_{10}[H_2W_{12}O_{42}]$, $(CetylPy)_4[W_{10}O_{32}]$ and $K_4[W_{10}O_{32}]$ and examples of the heteropolytungstic acids containing tungsten include $(CetylPy)_3[PW_{12}O_{40}]$, $(CetylPy)_5H_2[PW_{11}O_{39}]$ and $Na_9[PW_9O_{34}]$ and also those produced by replacing phosphorus (P) in the above-described heteropolytungstic acids with boron (B), silicon (Si) or germanium (Ge). $CetylNMe_3$ and CetylPy in the formulae represent cetyltrimethylammonium and cetylpyridinium, respectively.

Examples of the oxoacid containing molybdenum and salts thereof include compounds produced by replacing tungsten in the compounds exemplified above as oxoacid containing tungsten and salts thereof, with molybdenum. Examples of the oxoacid containing vanadium and salts thereof include compounds produced by replacing tungsten in the compounds exemplified above as the oxoacid containing tungsten and salts thereof, with vanadium.

Among these solid catalysts, preferred are catalysts selected from the group consisting of oxides of tungsten or molybdenum, isopolyacids containing tungsten or molybdenum and heteropolyacids containing tungsten or molybdenum and particularly preferred are catalysts selected from the group consisting of isopolyacids and heteropolyacids containing tungsten because a higher selectivity can be achieved with these catalysts.

Examples of the oxides, halides or sulfates of elements selected from the group consisting of iron, manganese and ruthenium include $FeCl_3$, $MnSO_4$ and $RuCl_3$.

The solid catalyst is not required to be immobilized to the solid catalyst support, and all what needs to be done is that the powdered solid catalyst is simply mixed with the powdered solid catalyst support. For example, the powdered solid catalyst is added in advance to the powdered solid catalyst support and then stirred and mixed thereby producing a mixture of the solid catalyst and solid catalyst support. No particular limitation is imposed on the particle sizes of the powdered solid catalyst and powdered solid catalyst support. Those having a particle size of about 5 to 100 μm, which are easily available may be used thereby achieving the advantageous effects of the present invention such as a higher yield of the product.

The amount of the solid catalyst is preferably 5 to 60 percent by mass, more preferably 10 to 50 percent by mass on the basis of the amount of the solid catalyst support. With 5 percent by mass or less of the catalyst, the compound represented by formula (1) cannot be produced at a high yield because the reaction rate is decreased. With more than 60 percent by mass of the catalyst, the yield cannot be improved, and thus it is industrially disadvantageous.

Next, to the mixture of the powdered solid catalyst support and the powdered solid catalyst produced as described above are added a compound having a carbon-carbon double bond to be oxidized and a hydrogen peroxide solution and optionally an organic solvent to be formed into a slurry, in which oxidation reaction is so carried out that the components are each dispersed and come into mutual contact. The formation of the slurry and the oxidation reaction are usually carried out mixing and stirring the raw materials and reaction product.

The hydrogen peroxide solution may be used in an amount of about 0.5 to 5 mmol as hydrogen peroxide on the basis of 1 mmol of the double bond site of (a), but the amount is desirously from 0.6 to 2.5 mmol. Less than 0.5 mmol of the hydrogen peroxide solution results in lack of hydrogen peroxide and thus in a decrease in the yield of the epoxy compound while more than 5 mmol of the hydrogen peroxide solution results in a decrease in the concentration of (a) and thus in a failure to produce the epoxy compound with good productivity.

The solid catalyst support and solid catalyst may be used in an amount of about 0.01 to 0.4 g on the basis of 1 mmol of (a) but desirously 0.05 to 0.2 g.

In the present invention, the hydrogen peroxide solution is used at a concentration of preferably 5 to 60 percent by mass, more preferably 5 to 35 percent by mass. In the case of using a hydrogen peroxide solution of a low concentration in a method for producing an epoxy compound using hydrogen peroxide, the produced epoxide is hydrolyzed to produce by-products such as diols and the like, resulting in the reduced selectivity of the intended product. However, the method of the present invention is high in selectivity and can produce the intended product at a higher yield even in the case of using a hydrogen peroxide solution of low concentration.

In the present invention the oxidation reaction is carried while the components are each dispersed in the slurry and contact with one another. In order to form a proper slurry, it is important to adjust the ratio of the solid powders and the solutions to a specific mass ratio. The total charge mass of (c) a powdered solid catalyst support and (d) a powdered catalyst for forming a slurry is 100 percent by mass or less, preferably within the range of 10 to 100 percent by mass on the basis of the total charge mass of (a) a compound having a carbon-carbon double bond, (b) a hydrogen peroxide solution and (e) an organic solvent. If the mass ratio is more than 100 percent by mass, a slurry may not be formed. If the mass ratio is less than 10 percent by mass, the reaction rate is reduced and thus the yield of an epoxy compound would be decreased.

The amount of the organic solvent to be used for forming a slurry is from 0 to 500 percent by mass, preferably 0 to 200 percent by mass on the basis of the mass of the compound having a carbon-carbon double bond. If the mass ratio exceeds 500 percent by mass, the productivity of an epoxy compound cannot be improved because the concentration of (a) would be reduced.

No particular limitation is imposed on (e) the organic solvent used in the present invention. Examples of the organic solvent include aliphatic hydrocarbons, aromatic hydrocarbons, alcohols, ethers, esters, amides, ketones, nitrile, sulfones, epoxides, and mixtures thereof. The organic solvent is preferably ethanol, ethyl acetate, hexane or toluene, more preferably toluene.

In the present invention, the oxidation reaction mode is not limited to a batch mode or a continuous mode but is preferably a batch mode. No particular limitation is imposed on the addition order of (a) to (e). The reaction may be carried out by adding (c) and (d) to (a) and (e) to form a slurry and then adding thereto dropwise (b). For the reaction in the present invention, it is important to suppress particles from settling and keep the contact efficiency of oil and water. The reaction is usually carried out stirring.

In the present invention, the oxidation reaction temperature is generally preferably from 0 to 50° C., more preferably 5 to 40° C. At lower than 0° C., the reaction proceeds slowly while at higher than 50° C., it causes the yield to decrease due to deactivation of the solid catalyst or ring-opening of the epoxides.

The reaction time is generally preferably from 1 to 24 hours, more preferably 1 to 12 hours. With a reaction time of shorter than 1 hour, the reaction does not proceed sufficiently and thus decreases the yield while with a reaction time of longer than 24 hours, the productivity decreases.

In the present invention, the conversion rate of olefin compounds is preferably 50% or greater, and the yield of an epoxy compound is preferably 30% or greater.

No particular limitation is imposed on the method for isolating the produced epoxy compound. For example, a method may be used wherein the epoxy compound is solvent-extracted and then concentrated.

The chlorine content of the epoxy compound produced by the present invention is preferably 100 ppm by mass or less, more preferably 10 ppm by mass or less because the compound when formed into a cured resin product can be further improved in moisture proof reliability. The chlorine content is the value measured in accordance with JIS K-7243-3, specifically the value measured by dissolving an epoxy compound in diethylene glycol monobutyl ether and saponifying the solution with a potassium hydroxide alcohol solution, heating it to reflux, followed by potentiometric titration with a silver nitrate solution.

The chlorine content of the epoxy compound can be reduced by purification by distillation, or alternatively by a method such as alkali aqueous solution washing or absorbent treatment.

The metal content of the epoxy compound produced by the present invention is preferably 100 ppm by mass or less, more preferably 10 ppm by mass or less because a cured resin product produced from the compound is further enhanced in mechanical characteristics and electrical characteristics. The metal content can be measured by analyzing a 10% toluene solution of an epoxy compound with inductively-coupled plasma emission (ICP emission). The apparatus for the measurement may be Optima 4300DV manufactured by Perkin-Elmer Corp. In this measurement, quantitative analysis of each metal species detected by qualitative analysis can be carried out using a commercially available metal standard solution.

The metal content of the epoxy compound can be reduced by purification by distillation, or alternatively by a method such as alkali aqueous solution washing or absorbent treatment.

EXAMPLES

The present invention will be described in more detail with the following examples but is not limited thereto.

Example 1

Into a screw-top test tube were weighed out 0.50 g of apatite that is a solid catalyst support and 0.085 g (0.015 mmol) of $(CetylPy)_9(NH_4)[H_2W_{12}O_{42}]$ that is a solid catalyst, followed by well-mixing. To the mixture were added 0.36 g (3.0 mmol) of tetrahydroindene and 0.64 g (6.6 mmol) of a 35% hydrogen peroxide solution. After the mixture was stirred at 20° C. for 6 hours, the resulting reaction mixture was extracted with toluene (1 mL×3 times) and the solvent was distilled out from the extracted solution thereby producing 0.27 g of tetrahydroindene diepoxide, which was a colorless transparent solution. The yield of the product (diepoxide yield) was 59%.

Example 2

Into a screw-top test tube were weighed out 0.50 g of apatite that is a solid catalyst support and 0.085 g (0.015 mmol) of $(CetylPy)_9(NH_4)[H_2W_{12}O_{42}]$ that is a solid catalyst, followed by well-mixing. To the mixture were added 0.36 g (3.0 mmol) of tetrahydroindene and 0.64 g (6.6 mmol) of a 35% hydrogen peroxide solution. After the mixture was stirred at 15° C. for 6 hours, the resulting reaction mixture was extracted with toluene (1 mL×3 times) and the solvent was distilled out from the extracted solution thereby producing 0.26 g of tetrahydroindene diepoxide, which was a colorless transparent solution. The yield of the product (diepoxide yield) was 56%.

Example 3

Into a screw-top test tube were weighed out 0.50 g of apatite that is a solid catalyst support and 0.085 g (0.015 mmol) of $(CetylPy)_9(NH_4)[H_2W_{12}O_{42}]$ that is a solid catalyst, followed by well-mixing. To the mixture were added 0.60 g (5.0 mmol) of tetrahydroindene and 0.87 g (9.0 mmol) of a 35% hydrogen peroxide solution. After the mixture was stirred at 20° C. for 6 hours, the resulting reaction mixture was extracted with toluene (1 mL×3 times) and the solvent was distilled out from the extracted solution thereby producing a crude product. The crude product was charged into a distillation still and distilled at a pressure of 2 mmHg thereby producing 0.43 g of tetrahydroindene diepoxide as a fraction at a column top temperature of 90° C. The yield of the product. (diepoxide yield) was 57%.

Example 4

Into a screw-top test tube were weighed out 0.50 g of apatite that is a solid catalyst support and 0.14 g (0.025 mmol) of $(CetylPy)_9(NH_4)[H_2W_{12}O_{42}]$ that is a solid catalyst, followed by well-mixing. To the mixture were added 0.60 g (5.0 mmol) of tetrahydroindene and 0.87 g (9.0 mmol) of a 35% hydrogen peroxide solution. After the mixture was stirred at 20° C. for 6 hours, the resulting reaction mixture was extracted with toluene (1 mL×3 times) and the solvent was distilled out from the extracted solution thereby producing a crude product. The crude product was charged into a distillation still and distilled at a pressure of 2 mmHg thereby producing 0.46 g of tetrahydroindene diepoxide as a fraction at a column top temperature of 90° C. The yield of the product (diepoxide yield) was 60%.

Example 5

Into a screw-top test tube were weighed out 0.50 g of apatite that is a solid catalyst support and 0.14 g (0.025 mmol) of $(CetylPy)_9(NH_4)[H_2W_{12}O_{42}]$ that is a solid catalyst, followed by well-mixing. To the mixture were added 0.60 g (5.0 mmol) of tetrahydroindene and 0.87 g (9.0 mmol) of a 35% hydrogen peroxide solution. After the mixture was stirred at 20° C. for 4 hours, the resulting reaction mixture was extracted with toluene (1 mL×3 times) and the solvent was distilled out from the extracted solution thereby producing a crude product. The crude product was charged into a distillation still and distilled at a pressure of 2 mmHg thereby producing 0.39 g of tetrahydroindene diepoxide as a fraction at a column top temperature of 90° C. The yield of the product (diepoxide yield) was 51%.

Example 6

Into a screw-top test tube were weighed out 0.50 g of apatite that is a solid catalyst support and 0.085 g (0.015 mmol) of $(CetylPy)_9(NH_4)[H_2W_{12}O_{42}]$ that is a solid catalyst, followed by well-mixing. To the mixture were added 0.90 g (7.5 mmol) of tetrahydroindene and 1.3 g (14 mmol) of a 35% hydrogen peroxide solution. After the mixture was stirred at 20° C. for 6 hours, the resulting reaction mixture was extracted with toluene (1 mL×3 times) and the solvent was distilled out from the extracted solution thereby producing a crude product. The crude product was charged into a distillation still and distilled at a pressure of 2 mmHg thereby producing 0.63 g of tetrahydroindene diepoxide as a fraction at a column top temperature of 90° C. The yield of the product (diepoxide yield) was 55%.

Example 7

Into a screw-top test tube were weighed out 0.50 g of apatite that is a solid catalyst support and 0.085 g (0.015 mmol) of $(CetylPy)_9(NH_4)[H_2W_{12}O_{42}]$ that is a solid catalyst, followed by well-mixing. To the mixture were added 0.60 g (5.0 mmol) of tetrahydroindene, 0.31 g of toluene and 0.87 g (9.0 mmol) of a 35% hydrogen peroxide solution. After the mixture was stirred at 20° C. for 6 hours, the resulting reaction mixture was extracted with toluene (1 mL×3 times) and the solvent was distilled out from the extracted solution thereby producing a crude product. The crude product was charged into a distillation still and distilled at a pressure of 2 mmHg thereby producing 0.40 g of tetrahydroindene diepoxide as a fraction at a column top temperature of 90° C. The yield of the product (diepoxide yield) was 53%.

Example 8

Into a stainless steel reaction vessel were added 75 g (0.63 mol) of tetrahydroindene and 38 g of toluene, followed by addition of 63 g of apatite that is a solid catalyst support and 11 g (0.0094 mol) of $(CetylPy)_9(NH_4)[H_2W_{12}O_{42}]$ that is a solid catalyst, stirring thereby forming a slurry. While the mixture was stirred at 20° C., 109 g (1.1 mol) of a 35% hydrogen peroxide solution was gradually added dropwise thereto. After the mixture was stirred at 20° C. for 6 hours, the reaction mixture was extracted with toluene (100 mL×3 times) and the solvent was distilled out from the extracted solution thereby producing a crude product. The crude product was charged into a distillation still and distilled at a pressure of 2 mmHg thereby producing 51 g of tetrahydroindene diepoxide as a fraction at a column top temperature of 90° C. The yield of the product (diepoxide yield) was 54%.

Comparative Example 1

Into a screw-top test tube were weighed out 0.50 g of apatite that is a solid catalyst support and 0.085 g (0.015 mmol) of $(CetylPy)_9(NH_4)[H_2W_{12}O_{42}]$ that is a solid catalyst, followed by well-mixing. To the mixture were added 0.12 g (1.0 mmol) of tetrahydroindene and 0.23 g (2.4 mmol) of a 35% hydrogen peroxide solution, followed by well-stirring. Thereafter, the mixture was allowed to stand at 15° C. After the mixture was allowed to stand at 15° C. for 3 hours, the resulting reaction mixture was extracted with hexane (5 mL×3 times) and the solvent was distilled out from the extracted solution thereby producing 0.15 g of tetrahydroindene diepoxide, which was a colorless transparent solution. The yield of the product (diepoxide yield) was 98%.

The diepoxide yields per volume of mixtures of (a) to (e) were as set forth in Table 1 below. The yield/volume of Examples 1 to 8 under reaction conditions where slurries were used is 0.20 or greater, and thus the reaction conditions defined by the present invention provide a higher productivity comparing those of the comparative example where the solid phase was used.

TABLE 1

|  | Volume of mixtures of (a) to (e) mL | Diepoxide yield g | Yield/Volume g/ml |
|---|---|---|---|
| Example 1 | 1.0 | 0.27 | 0.27 |
| Example 2 | 1.0 | 0.26 | 0.26 |
| Example 3 | 1.5 | 0.43 | 0.29 |
| Example 4 | 1.5 | 0.46 | 0.31 |
| Example 5 | 1.5 | 0.39 | 0.26 |
| Example 6 | 2.2 | 0.63 | 0.28 |
| Example 7 | 1.9 | 0.40 | 0.22 |
| Example 8 | 230 | 51 | 0.22 |
| Comparative Example 1 | 1.0 | 0.15 | 0.15 |

INDUSTRIAL APPLICABILITY

The present invention can produce an epoxy compound at a higher reaction rate and yield.

The invention claimed is:

1. A method for producing an epoxy compound by reacting a compound having a carbon-carbon double bond with hydrogen peroxide in the coexistence of (a) a compound having a carbon-carbon double bond, (b) a hydrogen peroxide solution, (c) a powdered solid catalyst support and (d) a powdered solid catalyst and optionally (e) an organic solvent wherein the total mass of (c) and (d) is 100 percent by mass or less on the basis of the total mass of (a), (b) and (e), wherein the solid catalyst is an isopolyacid containing tungsten and/or a salt thereof and the method comprises preparing a slurry by mixing the components (a) to (e) and allowing them to contact one another in the slurry.

2. The method for producing an epoxy compound according to claim 1 wherein the amount of the organic solvent is from 0 to 500 percent by mass on the basis of the amount of the compound having a carbon-carbon double bond.

3. The method for producing an epoxy compound according to claim 1 wherein the organic solvent is selected from the group consisting of aliphatic hydrocarbons, aromatic hydrocarbons, alcohols, ethers, esters, amides, ketones, nitrile, sulfones, epoxides, and mixtures thereof.

4. The method for producing an epoxy compound according to claim 1 wherein the solid catalyst support is selected from the group consisting of phosphates, diatomaceous earth, silica, alumina, kaolin, silica-alumina and calcium fluoride.

5. The method for producing an epoxy compound according to claim 1 wherein the solid catalyst support is apatite.

6. The method for producing an epoxy compound according to claim 1 wherein the epoxy compound is a compound represented by formula (1) below:

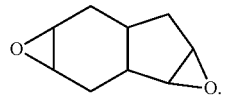
(1)

7. The method for producing an epoxy compound according to claim 1 wherein the solid catalyst is a isopolytungstic acid, a quaternary ammonium salt thereof, and/or pyridinium salt thereof.

8. The method for producing an epoxy compound according to claim 1 wherein the solid catalyst is selected from the group consisting of $(NH_4)_6W_7O_{24}$, $(NH_4)_{10}[H_2W_{12}O_{42}]$, $(CetylNMe_3)_7(NH_4)_3[H_2W_{12}O_{42}]$, $(CetylNMe_3)_{10}[H_2W_{12}O_{42}]$, $(CetylPy)_9(NH_4)[H_2W_{12}O_{42}]$, $(Cetyl)_{10}[H_2W_{12}O_{42}]$, $(CetylPy)_4[W_{10}O_{32}]$, and $K_4[W_{10}O_{32}]$.

* * * * *